United States Patent [19]
Peyman et al.

[11] Patent Number: 5,697,973
[45] Date of Patent: Dec. 16, 1997

[54] INTRAOCULAR SILICONE LENS

[76] Inventors: Gholam A. Peyman, 123 Walnut, New Orleans, La. 70118; Jeffery Koziol, 1211 S. Arlington Heights, Arlington Heights, Ill. 60005

[21] Appl. No.: 573,256

[22] Filed: Dec. 15, 1995

Related U.S. Application Data

[63] Continuation-in-part of Ser. No. 308,606, Sep. 19, 1994, abandoned.

[51] Int. Cl.⁶ .................................................. A61F 2/16
[52] U.S. Cl. .................................................. 623/6
[58] Field of Search .................................................. 623/6

[56] References Cited

U.S. PATENT DOCUMENTS

| | | | |
|---|---|---|---|
| Re. 33,039 | 8/1989 | Arnott | 623/6 |
| 4,124,905 | 11/1978 | Clark | 623/6 |
| 4,172,297 | 10/1979 | Schlegel | 623/6 |
| 4,206,518 | 6/1980 | Jardon et al. | 623/6 |
| 4,476,591 | 10/1984 | Arnott | 623/6 |
| 4,575,373 | 3/1986 | Johnson | 623/6 |
| 4,664,666 | 5/1987 | Barrett | 623/6 |
| 4,878,910 | 11/1989 | Koziol et al. | 623/6 |
| 5,133,750 | 7/1992 | Momose et al. | 623/6 |
| 5,171,320 | 12/1992 | Nishi | 623/6 |
| 5,201,763 | 4/1993 | Brady et al. | 623/6 |

FOREIGN PATENT DOCUMENTS

337390A2  10/1989  European Pat. Off.

*Primary Examiner*—Mary Beth Jones
*Attorney, Agent, or Firm*—Wood, Herron & Evans, LLP

[57] ABSTRACT

An intraocular lens (10, 60, 100) adapted to be fixated to the periphery of either the iris or an opening in the capsular bag has an annular ring (12) including an upper flange (14), a lower flange (16), and an interconnecting inner wall (18). Disposed within the annular (12) is a substantially circular lens (26). Alternatively, the intraocular lens includes a substantially circular lens (62) with a substantially U-shaped channel (64) extending inwardly along the perimeter of circular lens (62).

29 Claims, 3 Drawing Sheets

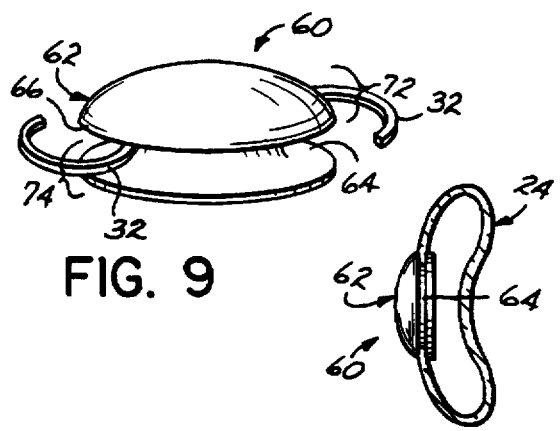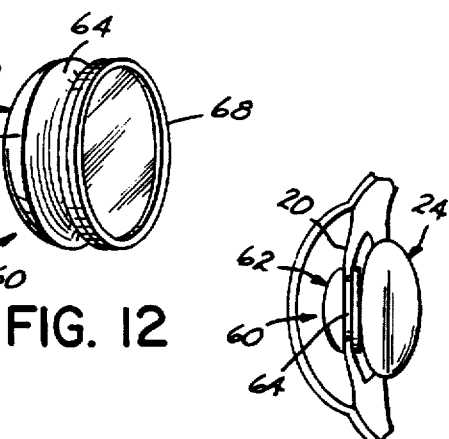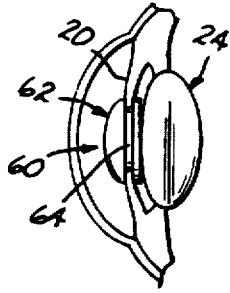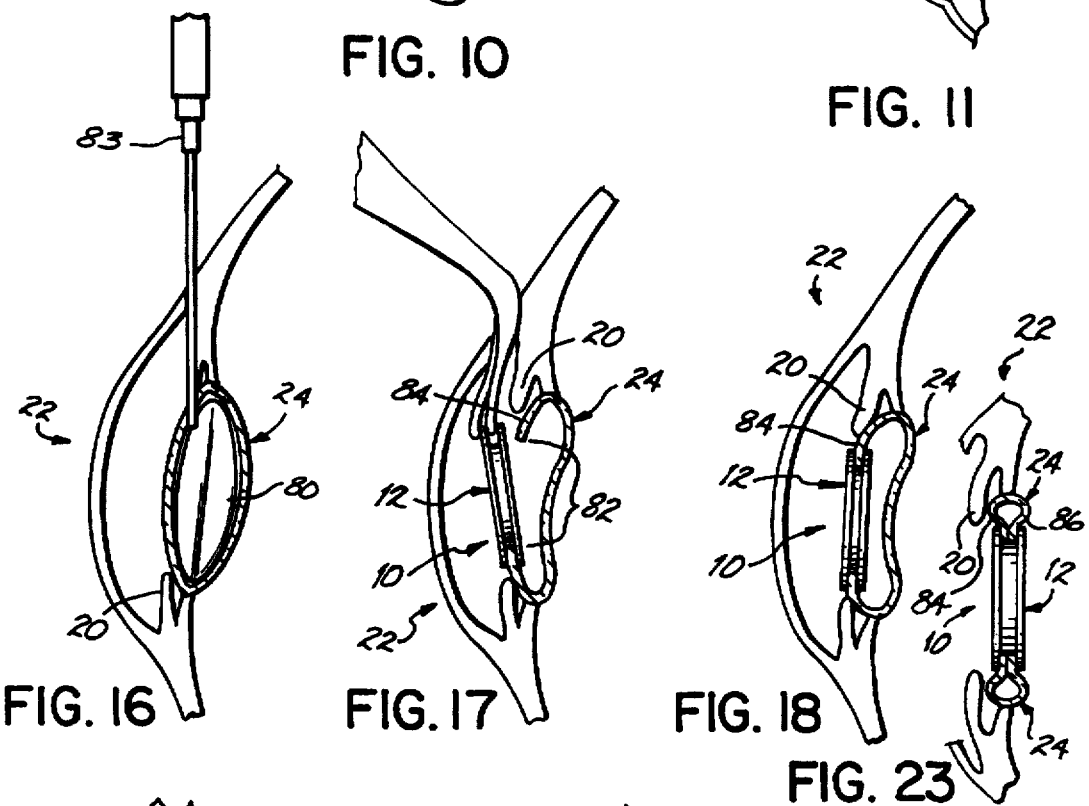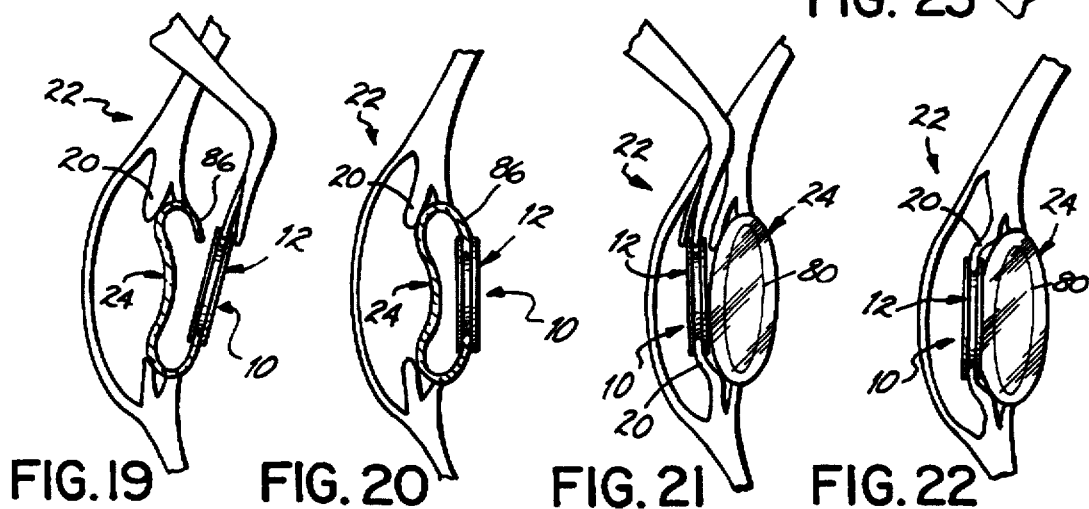

INTRAOCULAR SILICONE LENS

This is a continuation-in-part of Ser. No. 08/308,606 filed Sep. 19, 1994, with the United States Patent and Trademark Office, now abandoned.

FIELD OF THE INVENTION

The present invention relates generally to intraocular lenses, and more particularly, to an intraocular lens made from silicone that may be inserted into the iris of the eye or into an opening formed in the capsular bag.

BACKGROUND OF THE INVENTION

An intraocular lens is an artificial lens that is implanted into the eye of a patient to correct various problems associated with the patient's vision. For example, an intraocular lens may be implanted into the eye to correct high myopia, or nearsightedness, thereby alleviating the need for glasses or contact lenses. In another application, an intraocular lens may be inserted into the eye following removal of a cataract, which typically destroys the entire natural lens of the patient. Although existing intraocular lenses may be used in these applications, they suffer from many drawbacks.

Specifically, current intraocular lenses made from polymers cannot be fixated to the iris of eye, which cannot tolerate the stresses and strains caused by the weight of the lens. Further, current intraocular lenses fixated in the anterior chamber, which are used to correct myopia, touch the angle between the cornea and the iris, and may damage the cornea during use. Additionally, prior attempts to fixate an intraocular lens in the capsular bag have used a cross-like structure that depends upon the iris holding the lens in position. This type of lens also creates the possibility of damage to the iris during use of the lens.

Additionally, most existing intraocular lenses to be used after the removal of a cataract rely upon placement of the intraocular lens inside of the capsular bag. Typically they are fixated by outwardly extending spring-like members that embed into the walls of the capsular bag. However, during removal of a cataract, the capsular bag may be destroyed, thereby rendering unusable intraocular lenses that are designed for placement in the capsular bag.

Accordingly, there is a substantial need for an intraocular lens that may be used either in conjunction with the iris or the capsular bag, and which does not cause damage to the structures of the eye.

SUMMARY OF THE INVENTION

The present invention provides an intraocular lens adapted to receive either the periphery of the iris or an opening formed in the capsular bag which overcomes the drawbacks associated with existing intraocular lenses. More specifically, and in accordance with the present invention, an intraocular lens is provided that includes an integral annular ring having an outer upper flange, an outer lower flange, and an inner wall interconnecting the flanges wherein the flanges are spaced to receive therebetween the periphery of the iris or an opening in the capsular bag independent of additional support means, and a substantially circular lens whose perimeter is integrally formed with the inner wall of the annular ring such that the annular ring and circular lens are a single, unitary structure. The annular ring and lens are preferably flexible and may be manufactured from silicone. The intraocular lens may include fixation members where the lens is to receive the periphery of the iris. The lens may be a thin membrane having a plurality of concentric circular grooves therein, for using a plurality of concentrive annular prisms. Still further, a separate reinforcement ring may be attached to the annular ring to reduce the collapsibility of the intraocular lens. This reinforcement ring may be located along the lower flange of the annular ring, and preferably is manufactured from teflon, polymethymethacrylate, or a metal. Further, where the lens is a thin membrane, the reinforcement ring serves to maintain the lens in a planar orientation in use.

The radial dimension of the upper and lower flanges may be sized to accommodate the expansion and contraction of the iris of the eye. Further, the annular ring may have an outer diameter from about 3 millimeters to about 10 millimeters, and preferably having an outer diameter from about 5 millimeters to about 6 millimeters. Still further, the lens may have a diameter from about 2 millimeters to about 7 millimeters, and, more preferably, a diameter from about 3 millimeters to about 5 millimeters. If the lens is a thin membrane, Fresnel lens, the lens may have a diameter of from about 14 millimeters to about 15 millimeters.

To permit the free passage of intraocular fluid through the annular ring, a plurality of channels may be formed therein and extending therethrough.

The perimeter of the lens may be integrally formed with the inner wall of the annular ring by a plurality of circumferentially spaced apart tabs between the perimeter of the lens and the inner wall, wherein the tabs also form a plurality of openings therebetween that permit the free passage of intraocular fluid through the intraocular lens. Alternatively, the perimeter of the lens may be integrally formed along its entire length with the inner wall of the annular ring.

Depending upon the application, the flanges of the annular ring may have differing radial dimensions. Specifically, the lower flange may have a larger radial dimension than the upper flange, or the upper flange may have a larger radial dimension than the lower flange.

Alternatively, and in accordance with a further aspect of the present invention, an intraocular lens is provided that includes a substantially circular lens having a U-shaped annular channel extending inwardly along the perimeter thereof, wherein the channel is adapted to receive the periphery of the iris of an eye or an opening in the capsular bag independent of additional support means. Preferably, the lens is manufactured from a flexible polymer, such as silicone. The lens may also be a thin-membrane having a plurality of circular grooves therein, each forming a prismatic lens. Additionally, the lens may further include a separate reinforcing ring attached to the lens to reduce the collapsibility thereof. The intraocular lens may include fixation members where the lens is to receive the periphery of the iris.

The intraocular lens of the present invention may be used in several procedures. First, the intraocular lens may be used in repairing the vision of an eye that is blocked by a cataract. In use, an opening is made in the capsular bag of an eye. The cataract is extracted, and the intraocular lens adapted to engage the periphery of an opening in the capsular bag for support thereof is inserted into the capsular bag. Finally, the periphery of the opening in the capsular bag is engaged by the intraocular lens. The opening in the capsular bag to which the intraocular lens is fixated may be made in either the anterior capsule or the posterior capsule. Further, the cataract may be extracted by extracapsular cataract phacoemulsification of the lens followed by aspiration of the lens fragments.

Alternatively, the vision of an eye may be repaired by use of the intraocular lens of the present invention by inserting the intraocular lens adapted to engage the periphery of the iris of an eye for support thereof into the iris and engaging the periphery of the iris with the intraocular lens.

In another use for repairing the vision of an eye with the intraocular lens of the present invention, an opening is made in both the anterior capsule and the posterior capsule of the capsular bag. A first intraocular lens, which is adapted to engage the periphery of an opening in the capsular bag for support therefrom, is inserted into and engaged with the periphery of the opening in the anterior capsule. Next, a second intraocular lens, which is also adapted to engage the periphery of an opening in the capsular bag, is inserted into and engaged with the opening in the posterior capsule of the bag. Alternatively, a single intraocular lens in accordance with the present invention may be inserted into the periphery of both the opening in the anterior capsule and the opening in the posterior capsule followed by engaging both the periphery of the opening in the anterior capsule and the opening in the posterior capsule with the single intraocular lens.

By virtue of the foregoing, there is thus provided an intraocular lens adapted to receive either the periphery of the iris of an eye or the periphery of an opening in the capsular bag. These and other objects and advantages of the present invention shall become apparent from the accompanying drawings and the detailed description thereof.

BRIEF DESCRIPTION OF THE DRAWINGS

The accompanying drawings, which are incorporated in and constitute a part of this specification, illustrate embodiments of the invention and, together with a general description given above, and a detailed description given below, serve to explain the principles of the present invention.

FIG. 9 is another intraocular lens in accordance with the principles of the present invention;

FIG. 10 is a fragmentary view of a human eye illustrating the implantation of the intraocular lens of FIG. 9 in an opening in the capsular bag;

FIG. 11 is a fragmentary view of a human eye illustrating the implantation of the intraocular lens in the periphery of the iris;

FIG. 12 is a bottom perspective view of the intraocular lens of FIG. 9;

FIG. 16 is a fragmentary view of a human eye illustrating an incision in the capsular bag and the use of a phacoemulsification instrument to remove the natural lens of an eye;

FIG. 17 is a fragmentary view of a human eye illustrating the insertion of an intraocular lens in accordance with the principles of the present invention into an opening in the anterior capsule of the capsular bag;

FIG. 18 is a fragmentary view of a human eye illustrating the engagement of an intraocular lens in accordance with the principles of the present with the periphery of an opening in the anterior capsule of the capsular bag;

FIG. 19 is a fragmentary view of a human eye illustrating the insertion of an intraocular lens in accordance with the principles of the present invention into an opening in the posterior capsule of the capsular bag;

FIG. 20 is a fragmentary view of a human eye illustrating the engagement of an intraocular lens in accordance with the principles of the present invention with the periphery of an opening in the posterior capsule of the capsular bag;

FIG. 21 is a fragmentary view of a human eye illustrating the insertion of an intraocular lens in accordance with the principles of the present invention into the periphery of the iris;

FIG. 22 is a fragmentary view of a human eye illustrating the engagement of an intraocular lens in accordance with the principles of the present invention with the periphery of the iris of an eye;

FIG. 23 is a fragmentary view of a human eye illustrating the engagement of an intraocular lens in accordance with the principles of the present invention with the periphery of openings in both the anterior capsule and the posterior capsule;

DETAILED DESCRIPTION OF THE DRAWINGS

Figure 2:
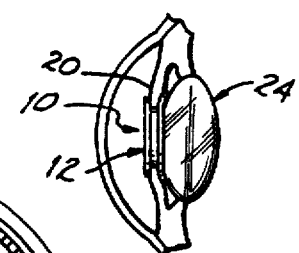
FIG. 2 is a fragmentary view of a human eye with the intraocular lens of FIG. 1 inserted in the opening of the iris.
Figure 1:
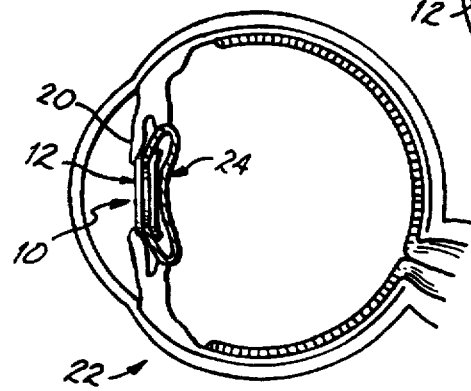
FIG. 1 is an anatomical illustration of the human eye with an intraocular lens of the present invention inserted in an opening in the capsular bag.

With reference to FIGS. 1–5, there is shown an intraocular lens 10 comprising an integral annular ring 12 having an outer upper flange 14, an outer lower flange 16, and an inner wall 18 interconnecting upper flange 14 and lower flange 16, which are spaced to receive therebetween the periphery of the iris 20 of an eye 22 (see FIG. 2) or an opening in the capsular bag 24 of an eye (see FIG. 1 ). A substantially circular lens 26 having a perimeter 28 formed with inner wall 18 of annular ring 12 completes intraocular lens 10.

Annular ring 12 and circular lens 26 are advantageously manufactured from a flexible, optically clear polymer, such as optically clear silicone as is well known in the art. Because silicone is lighter than water, intraocular lens 10 will, in effect, float within the eye following implantation therein. This is particularly advantageous when intraocular lens 10 is to be fixated to the iris 20 which cannot tolerate the stress or strain of supporting the weight of intraocular lens 10 without sustaining damage. Thus, an intraocular lens 10 made in accordance with the principles of the present invention may be fixated to the iris 20 without causing damage thereto. If intraocular lens 10 is to be fixated to an opening in the capsular bag 24, annular ring 12 and circular lens 26 may also be manufactured from optically clear silicone, but this is not necessary. In any event, the material selected should be flexible to aid in the insertion and engagement of intraocular lens 10 with the opening in the capsular bag 24. Any suitable biocompatible polymers, as are well known in the art, may be used in this application.

Figure 4:
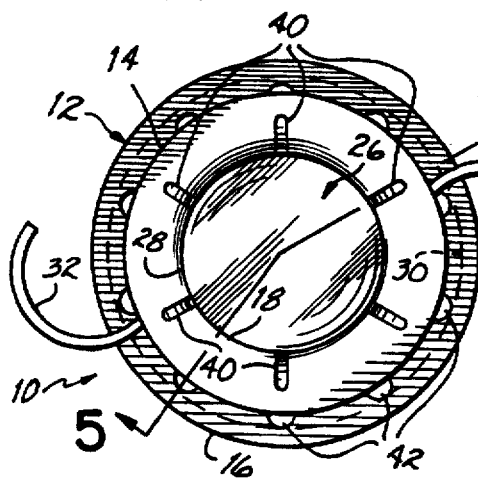
FIG. 4 is a top view of the intraocular lens of FIG. 3.
Figure 5:
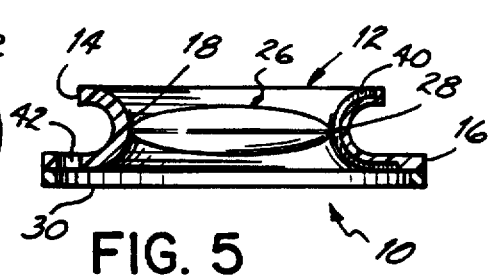
FIG. 5 is a cross-sectional view of the intraocular lens taken along line 5—5 of FIG. 4.

As intraocular lens 10 is preferably flexible it has been found advantageous to attach a separate reinforcement ring 30 to annular ring 12 to reduce the collapsibility of intraocular lens 10. This is particularly advantageous when intraocular lens 10 is to be fixated to an opening formed in the capsular bag 24 following removal of the natural lens to counterbalance the collapsing force of the capsular bag. As best seen in FIGS. 4 and 5, reinforcement ring 30 is shown attached to lower flange 16 along the perimeter thereof. However, as will be readily appreciated by those skilled in the art, reinforcement ring 30 may be placed attached along annular ring 12, including embedded therein. Reinforcement ring 30 may be manufactured from any suitable material having a higher stiffness than the material used for manufacturing annular ring 12 such as polyacrylate, methylmethacrylate, polymethylmethacrylate, teflon, or a metal ring embedded within annular ring 12.

Figure 3:
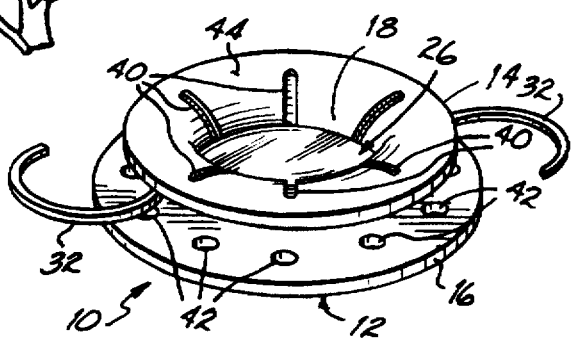
FIG. 3 is a top perspective view of an intraocular lens in accordance with the principles of the present invention.
Figure 8:
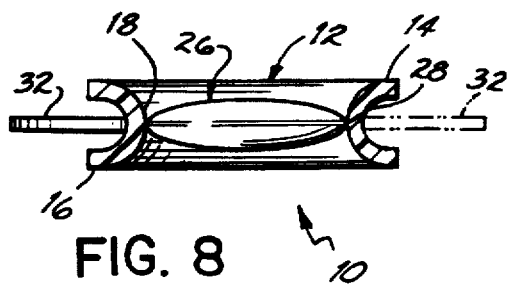
FIG. 8 is a sectional view similar to FIG. 5 but with the upper flange and lower flange having the same radial dimension.

Although intraocular lens 10 is preferably of a form not requiring additional support structure to fixate the lens, where intraocular lens 10 is to be fixated to the periphery of the iris 20 of the eye 22 some additional support means may be beneficial. To that end, and as shown in FIGS. 3, 4 and 8, intraocular lens 10 may include one or more fixation members 32 extending radially outwardly from inner wall 18 of annular ring 12. Fixation members 32 are flexible, C-shaped loops are as well known for attachment of intraocular lenses, and may be made from any number of flexible, biocompatible polymers such as polyacrylate, methylonethacrylate, or polymethyl methacrylate. As the iris 20 dilates and constricts, the iris 20 moves within annular ring 12. Although the periphery of the iris 20 remains at all times within annular ring 12, fixation members 32, which are embedded into the walls of iris 20 upon insertion, serve to support and stabilize intraocular lens 10. Fixation members 10 also improve the ease of insertion of intraocular lens 10. However, fixation members 32 are not a necessary component of the intraocular lens of the present invention. Additionally, although two fixation members 32 are shown, as will be readily appreciated by those skilled in the art, any number of fixation members may be used.

The perimeter 28 of circular lens 26 is formed with inner wall 18. Thus circular lens 26 and annular ring 12 comprise a unitary structure. As best seen in FIG. 4, circular lens 26 may be formed integrally along the entire length of perimeter 28 with inner wall 18. However, it has been found beneficial to permit the intraocular fluid to freely pass through intraocular lens 10. Accordingly, in this embodiment, a plurality of channels 40, 42 may be formed along the inside surface 44 of annular ring 12 and through lower flange 16, respectively. Channels 40 extend into annular ring 12, starting at upper flange 14, traveling along inside surface 44, and terminating at the lower flange 16. Channels 42 may be in the form of holes formed through lower flange 16. Together, channels 40, 42 permit intraocular fluid to freely pass through intraocular lens 10 between the anterior and posterior chambers of the eye 22.

Figure 6:
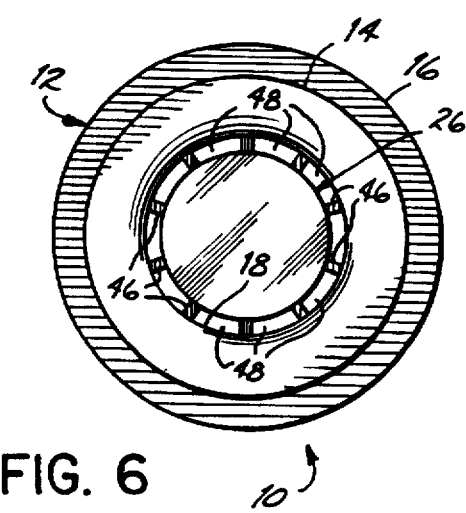
FIG. 6 is a top view of another intraocular lens made in accordance with the principles of the present invention.

Alternatively, and as best seen in FIG. 6, the perimeter 28 of circular lens 26 may be formed with inner wall 18 by a plurality of interconnecting tabs 46, which extend between the perimeter 28 circular lens 26 and inner wall 18. Tabs 46 are spaced circumferentially around circular lens 26, thereby forming a plurality of openings 48 between circular lens 26 and inner wall 18. In this embodiment, no additional channels need be formed in intraocular lens 10. Rather, the intraocular fluid is free to pass through the openings 48 in intraocular lens 10. Although intraocular lens 10 is shown with channels 40, 42, or openings 48 formed therein, it will be readily appreciated by those skilled in the art that intraocular lens 10 may be formed without any channels formed therein.

Figure 7:
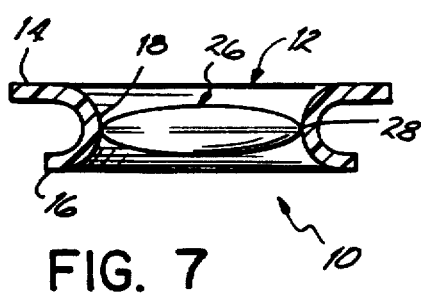
FIG. 7 is a sectional view similar to FIG. 5 but with the upper flange having a larger radial dimension larger than the radial dimension of the lower flange.

Referring to FIGS. 5, 7, and 8, the radial dimension of upper flange 14 and lower flange 16 may be of varying sizes. For example, as shown in FIG. 8, upper flange 14 and lower flange 16 may have the same radial dimension. Alternatively, lower flange 16 may have a greater radial dimension than upper flange 14, as shown in FIG. 5. Still further, upper flange 14 may have a larger radial dimension than lower flange 16, as shown in FIG. 7. Additionally, the sizes of upper flange 14 and lower flange 16 may vary from that depicted in the figures. For example, it may be advantageous when fixating intraocular lens 10 to an opening in the capsular bag 24, to form lower flange 16 so as to substantially fill capsular bag 24 in use. As will be readily appreciated by those skilled in the art, the selection of the sizes of the upper flange 14 and lower flange 16 will vary according to the procedure being performed and the intended function of intraocular lens 10. Accordingly, departures from the dimensions and proportions of the exemplary embodiments may be made without departing from the spirit or scope of the present invention.

Where intraocular lens 10 is to be fixated to the periphery of the iris 20, the radial dimension of upper flange and lower flange 16 should be sufficient to accommodate expansion and contraction of the iris of the eye. This will permit normal functioning of the eye without interference from intraocular lens 10. In general, annular ring 12 may have an outer diameter ranging from about 3 millimeters to about 10 millimeters, with circular lens 26 having a diameter from about 2 millimeters to about 7 millimeters. However, it has been found more advantageous to limit the outer diameter of annular ring 12 to from about 5 millimeters to about 6 millimeters, with the diameter of circular lens 26 ranging from about 3 millimeters to about 5 millimeters.

Although circular lens 26 is shown as a bi-convex lens in FIGS. 1–8, it will be readily appreciated by those skilled in the art that any suitable lens may be used in intraocular lens 10. For example, circular lens 26 may be bi-concave, planoconvex, planoconcave, convex-concave, diphractive bifocal, or torric (i.e., have variable surfaces for astigmatic correction), or any other known lens type.

With respect to FIGS. 9–12, there is shown another intraocular lens 60 in accordance with a further aspect of the present invention. Intraocular lens 60 comprises a substantially circular lens 62 having a substantially U-shaped annular channel 64 extending inwardly along the perimeter 66 of circular lens 62. U-shaped channel 64 is sized to receive therein either the periphery of the iris 20 of an eye 22 or the periphery an opening in the capsular bag 24 of an eye without the aid of separate anchoring structure.

As before, intraocular lens 60 may be manufactured from a flexible, optically clear polymer. Further, it has been found to be beneficial to manufacture intraocular lens 60 from optically clear silicone, such that intraocular lens 60 is lighter than water and, thereby, floats within the eye. This permits intraocular lens 60 to be fixated to the periphery of the iris 20 without damaging the iris in use. Additionally, and as best seen in FIG. 12, intraocular lens 60 may include a reinforcement ring 68 attached thereto along the lower surface 70 of intraocular lens 60 to reduce the collapsibility of intraocular lens 60. Reinforcement ring 68 may be made from any suitable material having a stiffness greater than that used for intraocular lens 60, such as polyacrylate, methylmethacrylate, polymethylmethacrylate, teflon, or a metal. Additionally, reinforcement ring 68 may be located anywhere in intraocular lens 60, including embedded therein. Still further, and as shown in FIG. 9, intraocular lens 60 may also include fixation members 32 as described above when intraocular lens 60 is to be fixated to the periphery of the iris 20.

Although intraocular lens 60 is shown having U-shaped channel 64 formed such that the diameter of the upper portion 72 of circular lens 62 and the diameter of the lower portion 74 of circular lens 62 are substantially the same, it will be readily appreciated by those skilled in the art that these diameters may vary depending upon the application to which intraocular lens 60 is intended. For example, if intraocular lens 60 is to be inserted into an opening in the capsular bag 24, lower portion 74 may be sized to substantially fill capsular bag 24. Alternatively, upper portion 72 may be sized to have a larger diameter than lower portion 74. These and other variations will be readily apparent to those skilled in the art.

Figure 13:
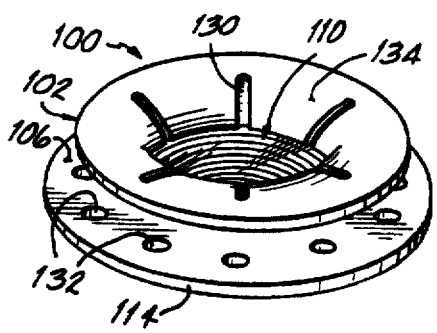
FIG. 13 is a top perspective view of another intraocular lens in accordance with the principles of the present invention.
Figure 14:
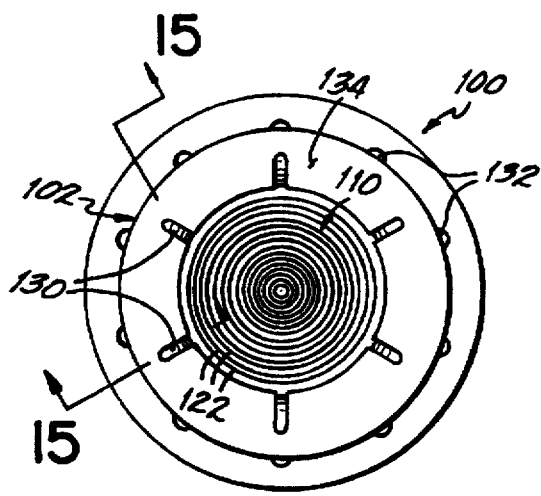
FIG. 14 is a top view of the intraocular lens of FIG. 13.
Figure 15:
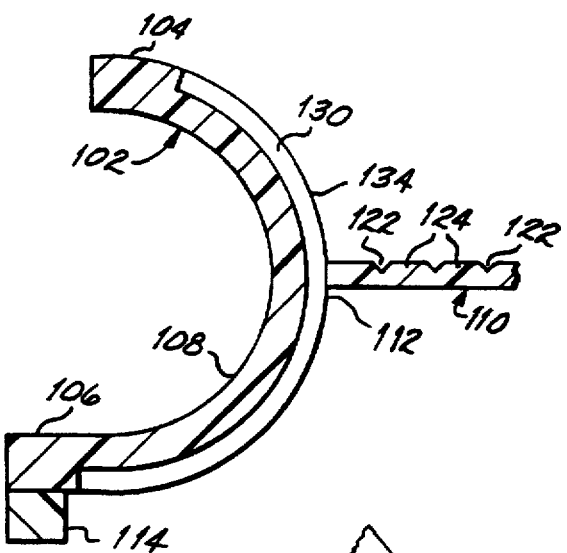
FIG. 15 is a partial cross-sectional view of the intraocular lens taken along line 15—15 of FIG. 14.

With reference to FIGS. 13–15, there is shown a still further intraocular lens 100 in accordance with a further aspect of the present invention. Intraocular lens 100 comprises an integral annular ring 102 having an outer upper flange 104, an outer flange 106, and an inner wall 108 interconnecting upper flange 104 and lower flange 106, which are spaced to receive therebetween the periphery of the iris of an eye or an opening in the capsular bag of an eye. A substantially circular lens 110 has a perimeter 112 formed with inner wall 108 of annular ring 102. A reinforcement ring 114 is attached to annular ring 102 for a purpose to be described below.

Lens 110 is manufactured from a flexible, optically clear polymer, such as optically clear silicone as is well known in the art. In contrast to traditional lenses, lens 110 comprises a thin membrane 120 having a plurality of concentric circular grooves 122 formed therein to create a plurality of concentric annular prisms 124, each of which is a separate lens. This type of lens is commonly referred to as a Fresnel lens. Circular grooves 122 may be formed by any known technology, such as through the use of an Xmer laser. Through this manufacturing technique, a large number of concentric prisms 124 may be manufactured on a single lens, such as on the order of 100 separate prismatic lenses 124.

As each of the separate prisms 124 forms an independent lens, membrane 120 may be extremely thin. However, due to the thinness of membrane 120, reinforcement ring 114 is required not only to reduce the collapsibility of intraocular lens 100 as in the other embodiments of the present invention, but also to maintain lens 110 in a planar orientation in use. Specifically, lens 110 must be maintained in a planar orientation to assure that each of concentric prisms 124 maintains its focal point at the proper position. To this end, reinforcement ring 114 is attached to annular ring 102 to stretch membrane 120 taut and maintain it in the desired planar configuration.

As with the other embodiments, annular ring 102 may include a plurality of channels 130, 132 formed along the inside surface 134 of annular ring 102 and through lower flange 106 respectively. Channels 40, 42 permit the intraocular fluid to freely pass through intraocular lens 100.

Due to the thinness of lens 110, intraocular lens 100 is particularly suited for applications wherein the existing biological lens is not removed. Specifically, intraocular lens 100 is particularly suited for use as an implanted lens to compensate for high myopia. However, intraocular lens 100 may also be used in circumstances where the biological lens is fully removed, as with the other embodiments of the present invention.

With reference to FIGS. 16–25, intraocular lens 10, 60, 100 may be inserted either into the periphery of the iris 20 or in the periphery of an opening formed in the capsular bag 24. Each possesses advantages depending upon the intended application. For example, if a cataract is being removed from the lens 80, it may be preferable to insert intraocular lens 10, 60, 100 in an opening formed in capsular bag 24 (see FIGS. 16–20 and 23). Alternatively, if it is desired only to correct the vision of the eye, such as to correct high myopia, it may be preferable to insert intraocular lens 10, 60, 100 into the periphery of the iris 20 (see FIGS. 21–22). Still further, if during removal of a cataract from the lens 80 the capsular bag 24 is completely destroyed, it may also be beneficial to place intraocular lens 10, 60, 100 into the periphery of the iris 20.

In use associated with removal of a cataract from an eye, and as shown in FIGS. 16–18, an opening 82 is made in the capsular bag 24. Although any opening may be made in conjunction with this procedure, capsular rhexis is preferred, as it forms a circular opening 82. Next, the cataract is extracted from the lens such as by extracapsular cataract phacoemulsification of the lens by a phacoemulsification instrument 83 followed by aspiration of the lens fragments as shown in FIG. 16. However, any acceptable procedure for removal of a cataract may be used. Next, as shown in FIG. 17, intraocular lens 10, 60, 100 is inserted into the opening 82 made in capsular bag 24. Finally, intraocular lens 10, 60, 100 is engaged with the periphery 85 of opening 82 in the capsular bag 24 (see FIG. 18).

Alternatively, opening 82 may be formed in the posterior capsule 86 and intraocular lens 1 0, 60, 100 inserted therein and engaged with the periphery of the opening in the posterior capsule 86, as shown in FIG. 19. Further, it may be preferable to form openings in both the anterior capsule 86 and the posterior capsule 88 followed by insertion of a first intraocular lens 10, 60, 100 in an opening in the anterior capsule 84 and a second intraocular lens 10, 60, 100 in an opening in the posterior capsule 86, as would be shown by a merging of FIGS. 17 and 19. Still further, a singular intraocular lens 10, 60, 100 may be inserted into and engage both the periphery of the opening in the anterior capsule 84 and the periphery of the opening in the posterior capsule 86 simultaneously as shown in FIG. 23.

In still a further aspect of the present invention, the vision of an eye may be repaired by inserting intraocular lens 10, 60, 100 in the periphery of the iris 20. As shown in FIGS. 21 and 22, intraocular lens 10, 60, 100 is inserted into the iris 20 of the eye 22. Next, the periphery of the iris 20 of the eye 22 is engaged with intraocular lens 10, 60, 100, thereby permitting correction of the vision of the eye 22. This procedure for implanting intraocular lens 10, 60, 100 may be used merely to correct the vision of the eye without removing the natural lens, such as where a person has high myopia. However intraocular lens 10, 60, 100 may be fixated to the iris 20 even where a cataract has been removed from the lens 80. Fixation to the iris is particularly advantageous where the capsular bag 24 has been destroyed during removal of a cataract.

Figure 24:
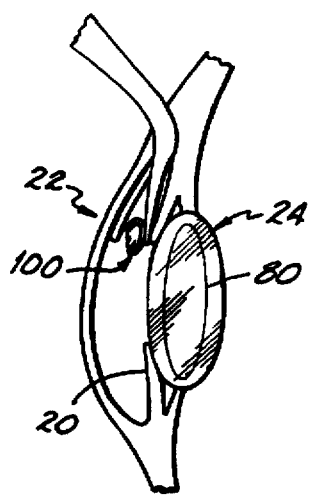
FIG. 24 is a fragmentary view of a human eye illustrating the insertion of an intraocular lens in accordance with the principles of the present invention between the iris and the capsular bag.
Figure 25:
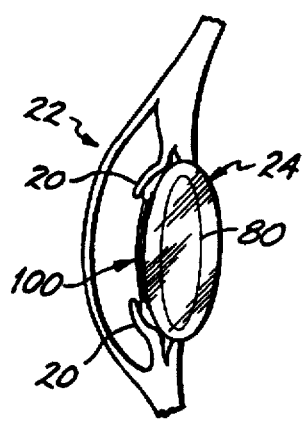
FIG. 25 is fragmentary view of a human eye illustrating the placement of an intraocular lens in accordance with the principles of the present invention between the iris of an eye and the capsular bag.

In a still further aspect of the present invention, the vision of an eye may be repaired by inserting intraocular lens 100 between the iris 20 and capsular bag 24. As shown in FIGS. 24 and 25, intraocular lens 100 is rolled up and inserted into the opening formed in the eye 22. Next, the lens is unrolled, with reinforcement ring 114 returning lens 110 to a planar configuration. Intraocular lens 100 is then positioned between iris 20 and capsular bag 24, thereby permitting correction of the vision of the eye 22. This specific procedure is particularly suited for correcting vision problems of the existing lens where replacement of the existing lens is not warranted, such as where the patient suffers from high myopia.

By virtue of the foregoing, there is thus provided an intraocular lens that may be fixated either to the periphery of the iris or to an opening in the capsular bag, and which does not cause damage to the structure of the eye.

While the present invention has been illustrated by description of different embodiments which have been described in considerable detail, it is not the intention of the Applicant to restrict or in any way limit the scope of the appended claims to such detail. Additional advantages will readily appear to those skilled in the art. Thus, the invention in its broadest aspects is not limited to the specific details, representative apparatuses and methods, and illustrative examples shown and described. Accordingly, departures may be made from the details without departing from the spirit or scope of Applicant's general inventive concept.

We claim:

1. An intraocular lens adapted to receive the periphery of the iris of an eye or an opening in the capsular bag of an eye comprising:
   an annular ring having an outer upper flange, an outer lower flange, and an inner wall interconnecting said flanges, said flanges being spaced to receive therebetween the periphery of the iris or an opening in the capsular bag of an eye; and
   a lens operatively interconnected to said inner wall, and wherein said lens is a thin membrane having a plurality of concentric circular grooves formed therein, said concentric rings forming a plurality of concentric annular prisms.

2. The intraocular lens of claim 1 wherein said annular ring and said lens are flexible.

3. The intraocular lens of claim 2 wherein said annular ring and said lens are manufactured from optically clear silicone.

4. The intraocular lens of claim further comprising a reinforcement ring attached to said annular ring to reduce the collapsibility of said intraocular lens, said reinforcement ring being manufactured from a material having a higher stiffness than the material from which said annular ring is manufactured.

5. The intraocular lens of claim 4 wherein said reinforcement ring is on said lower flange.

6. The intraocular lens of claim 4 wherein said reinforcement ring is made from teflon.

7. The intraocular lens of claim 4 wherein said reinforcement ring is made from polymethylmethacrylate.

8. The intraocular lens of claim 4 wherein said reinforcement ring is made from metal.

9. The intraocular lens of claim 1 wherein said upper flange and said lower flange have a radial dimension sufficient to accommodate expansion and contraction of the iris of the eye.

10. The intraocular lens of claim 9 further comprising a fixation member extending radially outwardly from said inner wall.

11. The intraocular lens of claim 1 wherein said annular ring has an outer diameter from about 3 millimeters to about 10 millimeters.

12. The intraocular lens of claim 10 wherein said annular ring has an outer diameter from about 5 millimeters to about 6 millimeters.

13. The intraocular lens of claim 1 wherein said lens has a diameter from about 2 millimeters to about 7 millimeters.

14. The intraocular lens of claim 11 wherein said lens has a diameter from about 3 millimeters to about 5 millimeters.

15. The intraocular lens of claim 1 wherein said lens has a diameter from about 14 millimeters to about 15 millimeters.

16. The intraocular lens of claim 1, said annular ring further including a plurality of channels extending therethrough to permit the free passage of intraocular fluid through said annular ring.

17. The intraocular lens of claim 1 wherein said perimeter of said circular lens is integrally formed with said inner wall by a plurality of circumferentially spaced apart tabs between said perimeter of said circular lens and said inner wall, said tabs forming a plurality of openings therebetween that permit the free passage of intraocular fluid therethrough.

18. The intraocular lens of claim 1 wherein said perimeter of said circular lens is integrally formed along the entire length thereof to said inner wall.

19. The intraocular lens of claim 1 wherein said flanges have differing radial dimensions.

20. An intraocular lens comprising:
   an integral annular ring having an outer upper flange, an outer lower flange, and an inner wall interconnecting said flanges, said flanges being spaced to receive therebetween the periphery of the iris or an opening in the capsular bag of an eye;
   a thin, optically clear membrane lens having a plurality of concentric circular grooves formed therein, said concentric circular grooves forming a plurality of annular prisms, said membrane lens having a perimeter formed with said inner wall; and
   a reinforcement ring attached to said integral annular ring to maintain said lens in a planar orientation in use.

21. The intraocular lens of claim 20 wherein said membrane has a diameter from about 14 millimeters to about 15 millimeters.

22. An intraocular lens adapted to receive the periphery of the iris of an eye or an opening in the capsular bag of an eye comprising:
   a substantially circular lens having a substantially U-shaped annular channel extending inwardly along the perimeter thereof, said channel being adapted to receive therein the periphery of the iris of an eye or an opening in the capsular bag of an eye and wherein said circular lens is a thin membrane having a plurality of concentric circular grooves formed therein, said concentric circular grooves forming a plurality of concentric annular prisms.

23. The intraocular lens of claim 22 wherein said circular lens is made from optically clear silicone.

24. The intraocular lens of claim 23 further including a reinforcement ring attached to said circular lens to reduce the collapsibility of said intraocular lens.

25. An intraocular lens adapted to receive the periphery of the iris of an eye or an opening in the capsular bag of an eye comprising:
   a flexible annular ring having an outer upper flange, an outer lower flange, and an inner wall interconnecting said flanges, said flanges being spaced to receive therebetween the periphery of the iris or an opening in the capsular bag of an eye;

a reinforcement ring attached to said annular ring, said reinforcement ring being manufactured from a material having a higher stiffness than the material from which said annular ring is manufactured; and a substantially circular lens operatively interconnected to said inner wall.

26. The intraocular lens of claim 25 wherein said reinforcement ring is made from teflon.

27. The intraocular lens of claim 25 wherein said reinforcement ring is made from polymethylmethacrylate.

28. The intraocular lens of claim 25 wherein said reinforcement ring is made from metal.

29. An intraocular lens adapted to receive the periphery of the iris of an eye or an opening in the capsular bag of an eye comprising:

an annular ring having an outer upper flange, an outer lower flange, and an inner wall interconnecting said flanges, said flanges being spaced to receive therebetween the periphery of the iris or an opening in the capsular bag of an eye;

a lens operatively interconnected to said inner wall; and a fixation member extending radially outwardly from said inner wall.

* * * * *

UNITED STATES PATENT AND TRADEMARK OFFICE
CERTIFICATE OF CORRECTION

PATENT NO.  : 5,697,973
DATED       : December 16, 1997
INVENTOR(S) : Gholam A. Peyman and Jeffery Koziol It is certified that error appears in the above-indentified patent and that said Letters Patent is hereby corrected as shown below:

Column 9, line 47, claim 4, after the word "claim"    insert --2--

Signed and Sealed this

Thirty-first Day of March, 1998

Attest:

BRUCE LEHMAN

Attesting Officer    Commissioner of Patents and Trademarks